US00PP16900P3

(12) United States Plant Patent
van der Voort

(10) Patent No.: US PP16,900 P3
(45) Date of Patent: Aug. 1, 2006

(54) LILY PLANT NAMED 'TIBER'

(50) Latin Name: *Lilium L.*
Varietal Denomination: Tiber

(75) Inventor: Cees A. van der Voort, Katwijk (NL)

(73) Assignee: VLetter & Den Haan Beheer B.V., Rijnsburg (NL)

( * ) Notice: Subject to any disclaimer, the term of this patent is extended or adjusted under 35 U.S.C. 154(b) by 0 days.

(21) Appl. No.: 09/357,097

(22) Filed: Jul. 19, 1999

(65) Prior Publication Data

US 2002/0083498 P1 Jun. 27, 2002

(51) Int. Cl.
*A01H 5/00* (2006.01)

(52) U.S. Cl. ..... Plt./315
(58) Field of Classification Search ..... Plt./315
See application file for complete search history.

(56) References Cited

PUBLICATIONS http://www.user.netland.nl/~hanns//exit4.html, Aalsmeer Horticultural Sites, pp. 1–6, see p. 3, citation for 'Tiber', May 5, 1996.*

UPOV–ROM GTITM Computer Database 2000/02, GTI Jouve Retrieval Software, citations for 'Tiber'.* http://www.user.netland.nl/~hanns//exit4.html, p. 2, May 1996.*

UPOV–ROM GTITM Computer Database 2000/02, GTI Jouve Retrieval Software, citation for 'Tiber', 1993.*

Copy of Dutch PBR Certificate NL 12590 for NL PBR LEL 0924. Feb. 11, 1993.

Copy of Belgium PBR Certificate BE LIU 1102 for BE PBR 24744. Sep. 15, 1994.

Copy of Chilean PBR Certificate CL 45/95 for CL PBR 00032. Nov. 17, 1995.

Copy of French PBR Certificate FR 7541 for FR PBR 150797. Mar. 7, 1994.

Copy of New Zealand PBR Certificate NZ 830 for NZ PBR LIL014. Mar. 24, 1994.

Copy of Polish PBR Certificate for PL 0 330 for PL PBR LI00029. Dec. 14, 1994.

Copy of German PBR Certificate for DE PBR LIU 00022. Nov. 1, 1993.

* cited by examiner

*Primary Examiner*—Anne Marie Grunberg
(74) *Attorney, Agent, or Firm*—Foley & Lardner, LLP

(57) ABSTRACT

A new and distinct cultivar of Lily plant named 'Tiber' characterized by having upright to horizontal flowers, intense, pink color, contrasting white tepal ends, and vigorous growth habit.

1 Drawing Sheet

BACKGROUND OF THE INVENTION

The present invention comprises a new and distinct cultivar of lily plant, botanically known as *Lilium L.,* and hereinafter referred to by the cultivar name 'Tiber'.

'Tiber' is a product of a planned breeding program which had the objective of creating new lily cultivars having large, upright flowers.

'Tiber' was originated from a hybridization made by the inventor in a controlled breeding program in Rijnsburg, the Netherlands in 1984. The male and female parents were unnamed seedlings of *Lilium L.* oriental hybrids. Both parents are proprietary cultivars used in the breeding program.

'Tiber' was discovered and selected as one flowering plant within the progeny of the stated cross by the inventor, Cees A. van der Voort, on Jun. 7, 1984 in a controlled environment in Rijnsburg, the Netherlands.

The first act of asexual reproduction of 'Tiber' was accomplished when scales were taken from the initial selection in October 1988 in a controlled environment in Rijnsburg, the Netherlands by, or under the supervision of, Cees A. van der Voort. Horticultural examination of selected units initiated in May, 1988 has demonstrated that the combination of characteristics as herein disclosed for 'Tiber' are firmly fixed and are retained through successive generations of asexual reproduction.

BRIEF DESCRIPTION OF THE INVENTION

The following traits have been repeatedly observed and are determined to be basic characteristics of 'Tiber' which, in combination, distinguish this lily as a new and distinct cultivar:

1. upright to horizontal flowers;
2. intense, pink color;
3. contrasting white tepal ends; and
4. vigorous growth habit.

'Tiber' has not been observed under all possible environmental conditions. The phenotype of the new cultivar may vary significantly with variations in environment such as temperature, light intensity, and daylength without any change in genotype. The following observations, measurements, and comparisons describe plants grown at the experimental research institute CPRO-DLO, Wageningen, the Netherlands under conditions which approximate those generally used in commercial practice.

Of the many commercial cultivars known to the present inventor, no other cultivars are similar in comparison to 'Tiber'.

BRIEF DESCRIPTION OF THE DRAWING

The accompanying color photographic drawing shows typical plant and flower characteristics of 'Tiber', with colors being as true as possible with illustrations of this type.

DETAILED BOTANICAL DESCRIPTION

In the following description, color references are made to The Royal Horticultural Society Colour Chart (R.H.S). The color values were determined between 12 am and 2 pm in May 1998 at the Dutch experimental research station CPRO-DLO, Wageningen, the Netherlands.

Origin: Seedling from breeding program.

Parentage:

*Female parent.*—Unnamed seedling.

*Male parent.*—Unnamed seedling.

Classification:

*Botanical.*—A hybrid of the genus *Lilium L.*

*Commercial.*—Oriental Lily cv. 'Tiber'.

Plant:

*Form.*—A single stem carrying numerous, alternately arranged pedicels.

*Height.*—Medium to high for the mature plant, approximately 85 cm.

*Growth habit.*—Vigorous; from the beginning of vegetation to the first flowering takes 90 days, depending on cultivation conditions, especially temperature i.e., approximately 20–30% more vigorous than the traditional 'Stargazer' cultivar.

*Stem.*—Circular in transverse section; anthocyanin pigmentation is present in spots and stripes; internodal length 6.5 cm, depending on the cultivation conditions of the cultivar.

*Foliage.*—Quantity: Approximately 60 to 70 depending on cultivation conditions. Size of leaf: Mature leaves are approximately 7.5 cm long and 2.5 cm wide. Shape of leaf: Generally ovate. Color: Medium green, RHS 136 A.

*Bulb.*—Size: 16 to 18 cm in circumference. Color: White RHS 157 B with pink shades.

Bud:

*Form.*—Tapering like a lancet.

*Size.*—11 cm in length depending on cultivation conditions.

*Opening.*—Unfolds normally.

*Color.*—Light pink, RHS 62A.

*Tepals.*—Folded, three visible.

Flower:

*Blooming habit.*—Raceme.

*Size.*—Medium, 20 cm in diameter depending on cultivation conditions.

*Borne.*—Upright to horizontal along a longitudinal axis.

*Shape.*—Generally, hexagonal star in form and bowl-shaped in cross-section.

*Tepalage.*—Number of Tepals: 6. Arrangement: Three inner and three outer. Color: RHS 64 A. Upper Surface: Pink, RHS 63C, mid-vein is green fading to yellow. Lower Surface: Light pink, RHS 62C. Spotting or Marking: Spots and markings are present, dark pink in color RHS 64A.

*Pedicel.*—Length: Short to medium, 8 cm, depending on cultivation conditions. Color: Secondary color on tepal tips and edges is white, RHS 155D. Form:

*Texture.*—Papillose.

*Disease resistance.*—Average in comparison to the disease resistance level of traditional Lily cultivars.

*Fragrance.*—Weak.

*Lasting quality.*—Excellent; 28 days under standardized storage condition, as compared to the general lasting quality of 21 days for the 'Stargazer' lily.

Reproductive organs:

*Stamens and anthers.*—Arrangements: Anthers form a generally circular pattern at their upper ends. Number: 6. Length: 7 cm depending on cultivation conditions. Filaments Color: Yellowish green, RHS 145 D.

*Pollen color.*—Dark brown, RHS 177 A.

*Anther color.*—Dark brown, RHS 200D.

*Pistils.*—Green, RHS 145 C.

*Stigma.*—Grey, RHS 201 B.

*Ovaries.*—Triangular in shape.

*Lasting quality.*—'Tiber' has an average lasting quality of 28 days, 7 days longer than the general lasting quality of lily plants under standardized storage conditions.

I claim:

1. A new and distinct cultivar of Lily plant named 'Tiber', as illustrated and described herein.

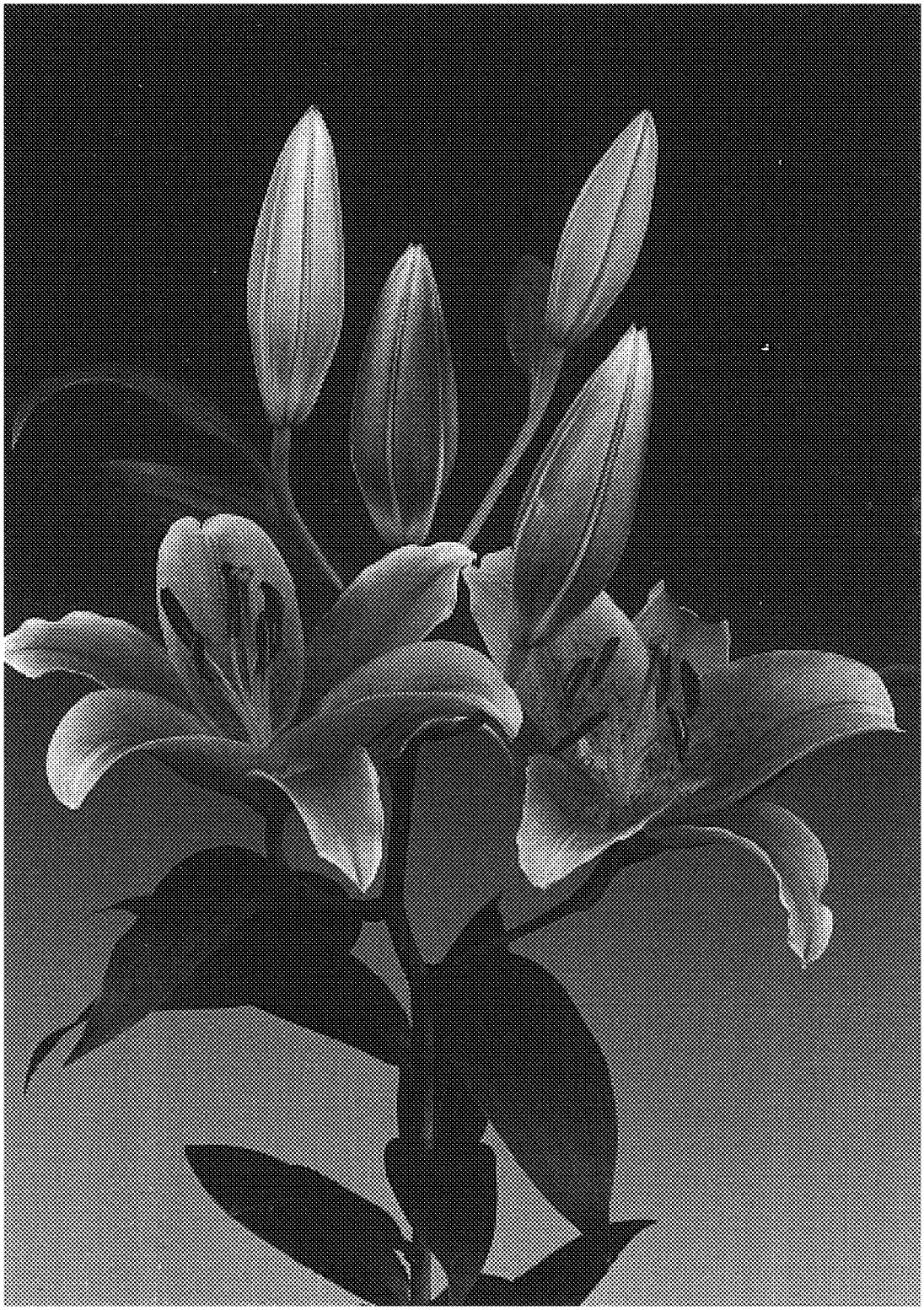

* * * * *